(12) United States Patent
Owen et al.

(10) Patent No.: US 6,569,891 B1
(45) Date of Patent: May 27, 2003

(54) **ANTIHYPERTENSIVE COMPOUND FROM *CAESALPINIA BRASILIENSIS***

(75) Inventors: Noel L. Owen, Provo, UT (US); Steven Glen Wood, Orem, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 09/979,376

(22) PCT Filed: May 19, 2000

(86) PCT No.: PCT/US00/13880

§ 371 (c)(1),
(2), (4) Date: May 2, 2002

(87) PCT Pub. No.: WO00/71115

PCT Pub. Date: Nov. 30, 2000

(51) Int. Cl.[7] .................. A61K 31/352; C07D 493/12
(52) U.S. Cl. .................. 514/453; 549/381; 536/4.1; 514/25
(58) Field of Search .................. 514/453, 25; 549/381; 536/4.1

(56) References Cited

PUBLICATIONS

Tokes, A.L. et al.: Absolute configuration and total synthesis of (−)–Cabenegrin A–1. Tetrahedron, vol. 55, pp. 9283–9296, 1999.*

"Account of Robert Burton regarding Potential Public Use of Palo De Brasil", 2 pages, Jul. 1995.

Tokes, A.L. et al.: Absolute Configuration and Total Synthesis of (−)–Cabenegrin A–1. Jul. 1999, vol. 55, pp. 9283–9296, especially compounds 1–12 on p. 9284.

* cited by examiner

Primary Examiner—Charanjit S. Aulakh
(74) Attorney, Agent, or Firm—Clayton, Howarth & Cannon, P.C.

(57) ABSTRACT

A compound isolated from an aqueous leachate of heartwood of "Palo de Brazil" *Caesalpinia brasiliensis* has antihypertensive activity. The compound was isolated by reversed-phase high pressure liquid chromatography to separate it from haematoxylin, which is co-extracted with the new compound. The compound is effective in reducing the blood pressure of hypertensive Sprague-Dawley rats.

7 Claims, 8 Drawing Sheets

ANTIHYPERTENSIVE COMPOUND FROM *CAESALPINIA BRASILIENSIS*

This application is a 371 of PCT/US00/13880 filed May 19, 2000, now WO 00/71115.

BACKGROUND OF THE INVENTION

This invention relates to a composition and methods for treating hypertension. More particularly, the invention relates to a compound purified from a water extract of Palo de Brazil (*Caesalpinia brasiliensis*), methods of making, and methods of using for treating hypertension.

Blood pressure is measured as systolic (pressure of the blood in the arteries when the heart beats) and diastolic (pressure between heartbeats). High blood pressure, or hypertension, is generally considered to be a pressure greater than or equal to 140 systolic and 90 diastolic (measured in millimeters of mercury). High blood pressure is a serious but modifiable risk factor for heart disease and stroke.

High blood pressure occurs when the body's smaller blood vessels (known as the arterioles) narrow, which causes the blood to exert excessive pressure against the vessel walls. The heart must therefore work harder to maintain this higher pressure. Although the body can tolerate increased blood pressure for months and even years, eventually the heart can enlarge and be damaged (a condition called hypertrophy), and injury to blood vessels in the kidneys, the brain, and the eyes can occur. Hypertension has been aptly called a silent killer, because it usually produces no symptoms.

Hypertension is referred to as essential, or primary, when the physician is unable to identify a specific cause. This is by far the most common type of high blood pressure, occurring in up to 95% of patients. Genetic factors appear to play a major role in essential hypertension. Several genetic factors, however, are probably involved that regulate important physiologic processes and interact with environmental influences to produce essential high blood pressure. Experts appear to have located the chromosomes (13 and 18) that house the genes responsible for blood pressure regulation, although pinning down the range of specific genes involved in hypertension is more difficult.

Secondary hypertension has recognizable causes, which are usually treatable or reversible. Causes of secondary hypertension include certain medical conditions, medications, alcohol, caffeine, and smoking. Medical conditions that contribute to temporary hypertension are pregnancy, cirrhosis, kidney disease, and Cushing's disease. Certain prescription and over-the-counter drugs can cause temporary high blood pressure. Some prescription medications include cortisone, prednisone, estrogen, and indomethacin. Long term use of nonsteroidal anti-inflammatory drugs (NSAIDs) may cause kidney damage and can also interfere with treatments for hypertension, including diuretics and beta-blockers. Such drugs include aspirin, ibuprofen (Advil, Motrin, Rufen), indomethacin (Indocin), naproxen (Anaprox, Naprosyn, Aleve), and many others. Of these drugs, aspirin appears to have the least detrimental effect on blood pressure. Cold medicines containing pseudoephedrine have also been found to increase blood pressure in hypertensive people, although they appear to pose no danger for those with normal blood pressure. High blood pressure is known to be an uncommon side effect in a few women taking oral contraceptives. Cocaine is known to cause acute episodes of hypertension, although apparently not chronic hypertension. An estimated 10% of hypertension cases are caused by alcohol abuse—three alcoholic drinks a day or more. Caffeine causes a temporary increase in blood pressure, which has been thought to be harmless in people with normal blood pressure. One study, however, suggested that long term and regular coffee drinking can boost blood pressure sufficiently to increase the risk for heart disease in healthy men. The dangers of caffeine on blood pressure, however, pale next to the risks from smoking. One study reported that smokers have blood pressures up to 10 points higher than nonsmokers. Although cigar smoking does not appear to cause coronary artery disease, it can double the risk of death from cardiomyopathy and hypertension. Temporary high blood pressure can also result from stress, exercise, and long-term consumption of large amounts of licorice. Exposure to even low lead levels also appears to cause hypertension in adults. One small study showed that mobile phone use triggers a temporary rise in blood pressure, which may be harmful in people with existing hypertension.

Only 27% of American adults with high blood pressure have it under control; about the same percentage is on medications but not controlling their blood pressure, and nearly 15% of those with hypertension are not on medication at all. Aggressive drug treatment of long-term high blood pressure can significantly reduce the incidence of death from heart disease and other causes in both men and women. In people with diabetes, controlling both blood pressure and blood glucose levels prevents serious complications of that disease. If patients have mild hypertension and no heart problems, then lifestyle changes may suffice if carried out with determination. For more severe hypertension or for mild cases that do not respond to changes in diet and lifestyle within a year, drug treatment is usually necessary. A single-drug regimen can often control mild to moderate hypertension. More severe hypertension often requires a combination of two or more drugs.

Dozens of antihypertensive drugs are available. They usually fall into the categories of diuretics, which cause the body to excrete water and salt; ACE inhibitors, which reduce the production of angiotensin, a chemical that causes arteries to constrict; beta-blockers, which block the effects of adrenaline, thus easing the heart's pumping action and widening blood vessels; vasodilators, which expand blood vessels; and calcium channel blockers, which help decrease the contractions of the heart and widen blood vessels. Research now indicates that beta-blockers, diuretics, and ACE inhibitors all reduce the risk for fatal and nonfatal cardiovascular events. As first-line treatment experts generally recommend beta-blockers or diuretics, which are inexpensive, safe, and effective, for most people with hypertension who have no complicating problems. Certain individuals, however, may have special requirements that call for specific drugs or combinations. All drugs used for hypertension have side effects, some distressing, and on-going compliance is difficult.

Plants have provided mankind with a valuable resource of unique and novel chemical compounds that have shown a wide variety of biological activities and have been used to treat a myriad of ailments. Ethnobotanical sources, such as modern and ancient herbals or carefully conducted interviews with indigenous healers and native shaman, have proven to be very effective means of identifying those plants of greatest medicinal importance. Some representative compounds discovered using documented ethnobotanical methodology include digitoxin (cardiac anti-arrhythmetic), turbocurarine (muscle relaxant), quinine (anti-malarial), and morphine (analgesic).

Surprisingly, 25% of all the prescription drugs in the United States in 1982 were extracted from plants. N. R. Farnsworth et al., 39 Econ. Bot. 231 (1985). In addition, over half of the current prescription drugs used in the United States are modeled after bioactive compounds originally found in plants. Id. Today, 80% of the world's population still relies solely on plants for medication. M. J. Balick & P. A. Cox, Plants, People, and Culture (Scientific American Library, New York, N.Y., 1996). Public awareness of the medicinal value of natural products is evidenced by the fact that the last ten years has seen an explosive growth in the sale of herbal products in the United States as over-the-counter nutritional supplements.

Furthermore, advancements in synthetic organic chemistry have made it possible to synthesize not only newly identified natural products, but also structural analogs and semi-synthetic derivatives. It was not until the beginning of the twentieth century that organic chemistry had developed sufficiently to make synthetic drugs widely available. One of the first, and most notable, of these compounds was aspirin, acetylsalicylic acid, synthesized in 1899. E. S. Ayensu et al., Our Green and Living World (Smithsonian Institute Press, Washington, D.C., 1984). This synthetic compound was based on salicylates isolated from willow bark. G. Weissman, Scientific American 84 (January 1991). Today, it is estimated that Americans consume 16,000 tons of aspirin each year. Since 1899, synthetic natural products along with numerous analogs have resulted in many prescription medications, some with enhanced bioactivity over the natural product. Even with all the advances in synthetic organic chemistry, however, much time and effort is saved by using a model compound established through the elucidation of a novel natural product.

Isolation of natural products has now expanded to include marine organisms (primarily snails and sponges), fungi, bacteria, insects, and arthropods, and the number of newly reported compounds is growing rapidly. Although a number of plants have been well characterized, the plant kingdom still presents an essentially untouched reservoir of compounds of unparalleled structural diversity. Of the 250,000 to 750,000 plant species estimated to exist, only 0.01% of these have been exhaustively studied for biological activity. M. J. Balick & P. A. Cox, supra.

Traditional ethnobotanical sources are an effective means of finding, isolating, and identifying previously unknown biological compounds. Knowledgeable healers are often able to provide the common name and location of a local plant, a supply of plant tissue, extraction procedures, dosage levels, and diseases that can be effectively treated. This information helps to promote efficient identification of the bioactive component.

In view of the foregoing, it will be appreciated that providing a new antihypertensive drug and methods of use and making thereof would be significant advancements in the art.

BRIEF SUMMARY OF THE INVENTION

It is an object of the present invention to provide a composition useful for treating high blood pressure.

It is another object of the invention to provide a method of isolating such an antihypertensive composition.

It is a further object of the invention to provide a method of making such an antihypertensive composition.

It is still another object of the invention to provide a method of treating hypertension.

These and other objects can be addressed by providing a purified compound having the formula:

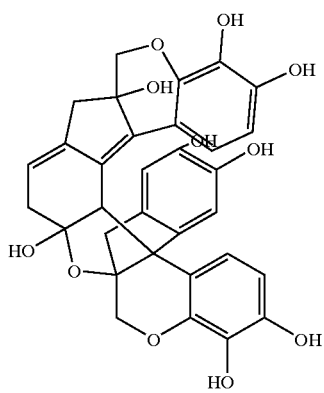

A method for isolating a compound having the formula:

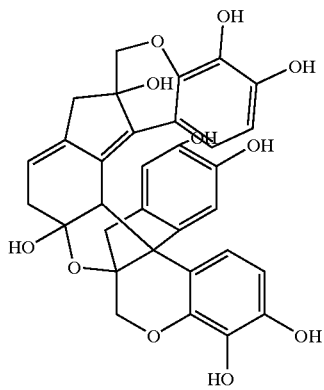

comprises:
(a) obtaining an aqueous leachate from *Caesalpinia brasiliensis*;
(b) fractionating the leachate by reverse-phase high performance liquid chromatography; and
(c) selecting a fraction substantially free of haematoxylin and having an activity for reducing blood pressure in hypertensive Sprague-Dawley rats. Preferably, the aqueous leachate is from heartwood of *Caesalpinia brasiliensis*.

A method for treating hypertension comprises administering an effective amount of a purified compound having the formula:

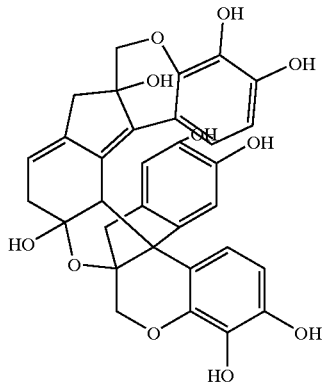

Another aspect of the present invention relates to a composition comprising an admixture of an effective amount of a purified compound represented by the formula:

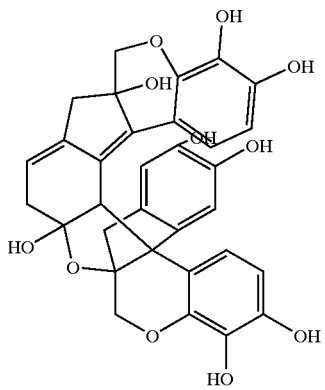

and a pharmaceutically acceptable carrier.

DETAILED DESCRIPTION

Figure 1:
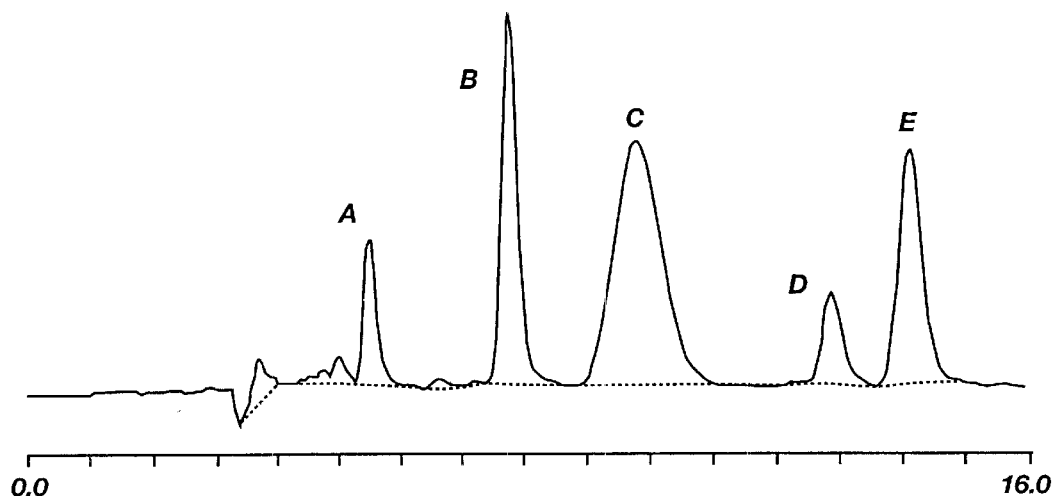
FIG. 1 shows an HPLC chromatogram of a water extract of *Caesalpinia brasiliensis*

Before the present composition, method for making thereof, and method for treating hypertension are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a composition comprising "a pharmaceutically acceptable carrier" includes reference to two or more of such pharmaceutically acceptable carriers.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "effective amount" means an amount of a drug or pharmacologically active agent that is nontoxic but sufficient to provide the desired local or systemic effect and performance at a reasonable benefit/risk ratio attending any medical treatment. An effective amount of the compound of the present invention is an amount sufficient to reduce the systolic blood pressure of an individual to a selected level.

As used herein, "purified" means separated from other molecules to the extent that the compound of the present invention appears as a single peak when analyzed by HPLC on a C-8 reverse phase Rainin Microsorb-mv (5 μm particle size, 100 Å pore size) analytical column (4.6×250 mm), using HPLC grade water and acetonitrile, both acidified with 0.1% trifluoroacetic acid, as a sample solvent system, and at a 10% acetonitrile isocratic gradient for elution.

As used herein, "substantially free of haematoxylin" means that no peak corresponding to haematoxylin is present when analyzed by HPLC on a C-8 reverse phase Rainin Microsorb-mv (5 μm particle size, 100 Å pore size) analytical column (4.6×250 mm), using HPLC grade water and acetonitrile, both acidified with 0.1% trifluoroacetic acid, as a sample solvent system, and at a 10% acetonitrile isocratic gradient for elution.

As used herein, "administering" and similar terms mean delivering the composition to the individual being treated such that the composition exerts its pharmacological effect of reducing blood pressure. Thus, the composition is preferably administered to the individual by systemic administration, typically by oral administration, for example, as a powder, capsule, tablet, or liquid. Suitable excipients include, for example, water, saline, dextrose, glycerol, and the like. If desired, minor amounts of auxiliary substances such as buffers and the like can be added.

As used herein, such a "pharmaceutically acceptable" component is one that is suitable for use with humans and/or animals without undue adverse side effects (such as toxicity, irritation, and allergic response) commensurate with a reasonable benefit/risk ratio. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers. Those skilled in the art will be able to select the best method of administration, for example as a powder, capsule, tablet, or liquid, using the information set forth herein.

As used herein, "COSY" means correlation spectroscopy. COSY is used for determining proton-proton scalar coupling. This technique produces a two-dimensional spectrum with both the axis and ordinate labeled by the chemical shift of the observed nucleus (most often a proton). Cross peaks, or off-diagonal peaks, indicate the presence of scalar coupling between the nuclei whose chemical shifts determine the location of the cross peak. The peaks along the diagonal reproduce the one-dimensional spectrum.

As used herein, "DEPT" means distortionless enhancement by polarization transfer. DEPT allows for the identification of the degree of saturation of each carbon. This technique involves the detection of proton magnetization and the subsequent transfer of this magnetization to the carbon it is directly coupled to. By altering the final proton pulse width, θ, various types of spin systems can be detected. A θ of 90 degrees will produce a spectrum in which only methine carbons appear. A θ of 135 degrees will produce a spectrum in which methine and methyl carbons are positive while methylene carbons are negative. Quaternary carbons will never give a signal because polarization transfer is impossible.

As used herein, "HETCOR" means heteronuclear correlation spectroscopy. HETCOR detects proton-carbon scalar coupling and identifies individual proton carbon attachments. This technique is much like COSY except that one of the axes in the resultant two-dimensional spectrum is labeled by the carbon chemical shift, while the other remains labeled by the hydrogen chemical shift.

As used herein, "HMBC" means multiple bond heteronuclear multiple quantum coherence (HMQC). HMQC determines proton-carbon scalar coupling. This technique involves carbon polarization transfer to hydrogen with observation of the proton signal. Delay, $1/(2\pi J)$, is set using a J value of approximately 140 Hz. This is the value of one bond hydrogen-carbon scalar coupling interactions. The only parameter that distinguishes HMBC from HMQC is that the J value is set to about 10 Hz. This is the value of multiple bonds (2–3 bonds) hydrogen-carbon scalar coupling interactions. Therefore, the long-range $^1H$–$^{13}C$ connectivities are detected by this technique.

EXAMPLE 1

About 300 g of the heartwood of *C. brasiliensis*, purchased from Pharmacia Gonzalez (Ponce, Puerto Rico) was ground to a find powder in a Wiley mill and exhaustively extracted with water. Removal of the water yielded about 10 g of solid residue. Analytical HPLC separation of this heartwood water extract was performed using a Rainin HPLC system with Dynamax pumps (63.5 cm (25 in.) head size) and Dynamax UV/VIS detector. A C-8 reverse phase Rainin Microsorb-mv (5 μm particle size, 100 Å pore size) analytical column (4.6×250 mm) with guard was used. HPLC grade water and acetonitrile, both acidified with 0.1% trifluoroacetic acid, were used as the solvent system. Samples were prepared by dissolving 100 mg of powdered extract in 3 ml of solvent, allowing the solution to stand for 2.5 hours, drying a 200 μl aliquot of the solution, and then dissolving the dried aliquot in 1 ml of water and immediately injecting 20 μl of the resulting solution into the analytical HPLC system at a 10% acetonitrile isocratic gradient. This analytical HPLC separation revealed several major peaks and many minor peaks (FIG. 1). The major peaks were labeled A, B, C, D, and E.

EXAMPLE 2

The crude extract and HPLC fractions prepared according to the procedure of Example 1 (with a preparative-scale (21.4×250 mm) column), were tested for antihypertensive activity by adding the sample to be tested at a concentration of 100 μg/ml to the drinking water of hypertensive Sprague-Dawley rats. After 36 hours, systolic blood pressures were measured with a Harvard tail cuff apparatus attached to a Beckman R511A recorder.

Figure 2:
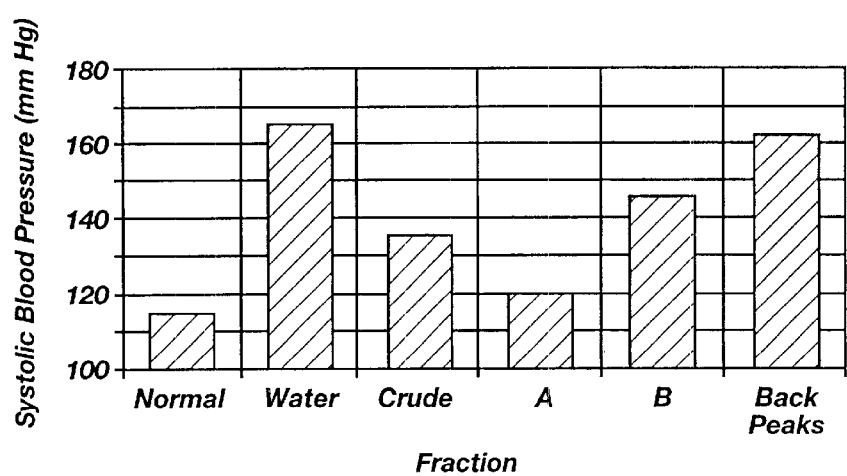
FIG. 2 shows the antihypertensive activities of fractions identified in the HPLC trace of FIG. 1 as compared to controls.

FIG. 2 shows the results of these tests, wherein "Normal" represents the blood pressure of non-hypertensive rats, "Water" represents the blood pressure of hypertensive rats given water without extract, "Crude" represents the blood pressure of hypertensive rats given the crude (unfractionated) extract, and "A," "B," and "Back Peaks" represent the respective blood pressure measurements obtained from rats given HPLC fraction A, B, or combined peaks C, D, and E. These results show that peak A reduced systolic blood pressure about 35%, thus bringing it into the normal range of 110–120 mm Hg. Peak B showed moderate activity, yielding about a 12% reduction in systolic blood pressure. The combined peaks C, D, and E ("Back Peaks") exhibited little activity. Peaks B and D were identified as haematoxylin and brazilin, respectively.

Approximately 50% of the total crude extract was determined to be haematoxylin identified in FIG. 1 at peak B. Brazilin, identified in FIG. 1 at peak D, comprised only about 6% of the total crude extract and slowly converted to haematoxylin in hot water. Peak A, the most active and most polar of these compounds, eluted early, making it easily obtainable. Peak A or "Palo A," however, only accounted for about 5–10% of each extraction, hence numerous preparative HPLC runs were required to isolate and purify enough material for characterization.

EXAMPLE 3

In this Example, mass spectral analysis of Palo A, purified according to the procedure of Examples 1 and 2, was performed. Mass spectral data were obtained on a Jeol SX 102A double focusing reverse geometry high resolution mass spectrometer using FAB-Xenon methodology in a standard sodiated thioglycerol matrix and standard software. Mass spectral analysis of Palo A showed the molecular ion $[M+1]^+$ to be at 601 mass units. Under high resolution conditions, this mass of 600 corresponds to a molecular formula of $C_{32}H_{24}O_{12}$ (−1.1/−0.7). This formula yields an index of unsaturation of 21. A second peak of 583 mass units, corresponding to a possible loss of a hydroxyl group, was also observed. Several other large peaks were also visible, indicating the presence of many degradation fragments.

EXAMPLE 4

NMR spectral data were obtained at ambient temperature in DMSO-$d_6$ on a Varian VXR-500S spectrometer using a standard 5 mm NMR tube. Standard Varian pulse sequences, software, and parameters were used. Computer estimations of $^{13}C$ shift data were obtained using ACD/CNMR datatables software, version 2.51.

Figure 3:
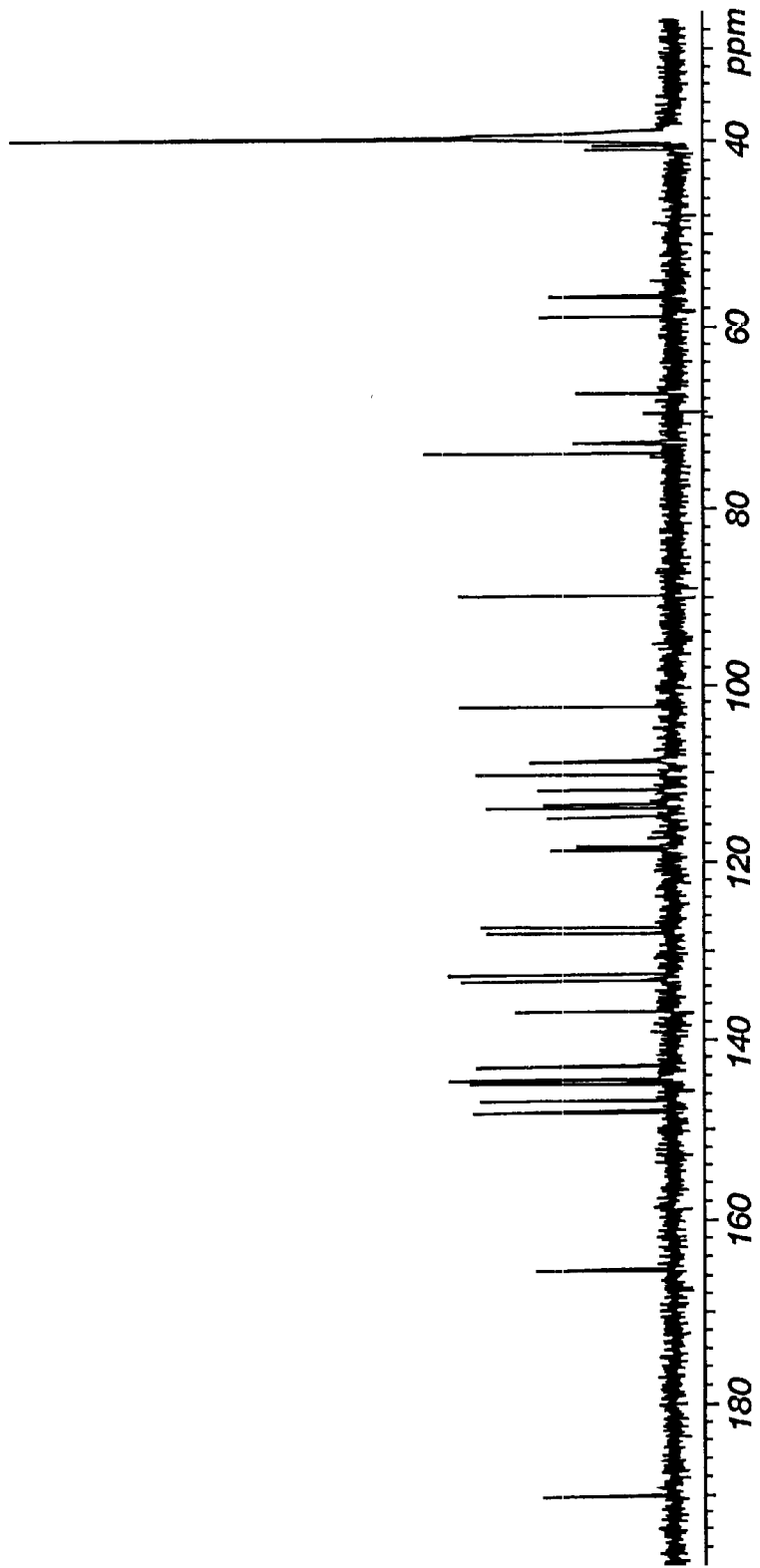
FIG. 3 shows a $^{13}$C spectrum of the composition of the present invention.
Figure 4:
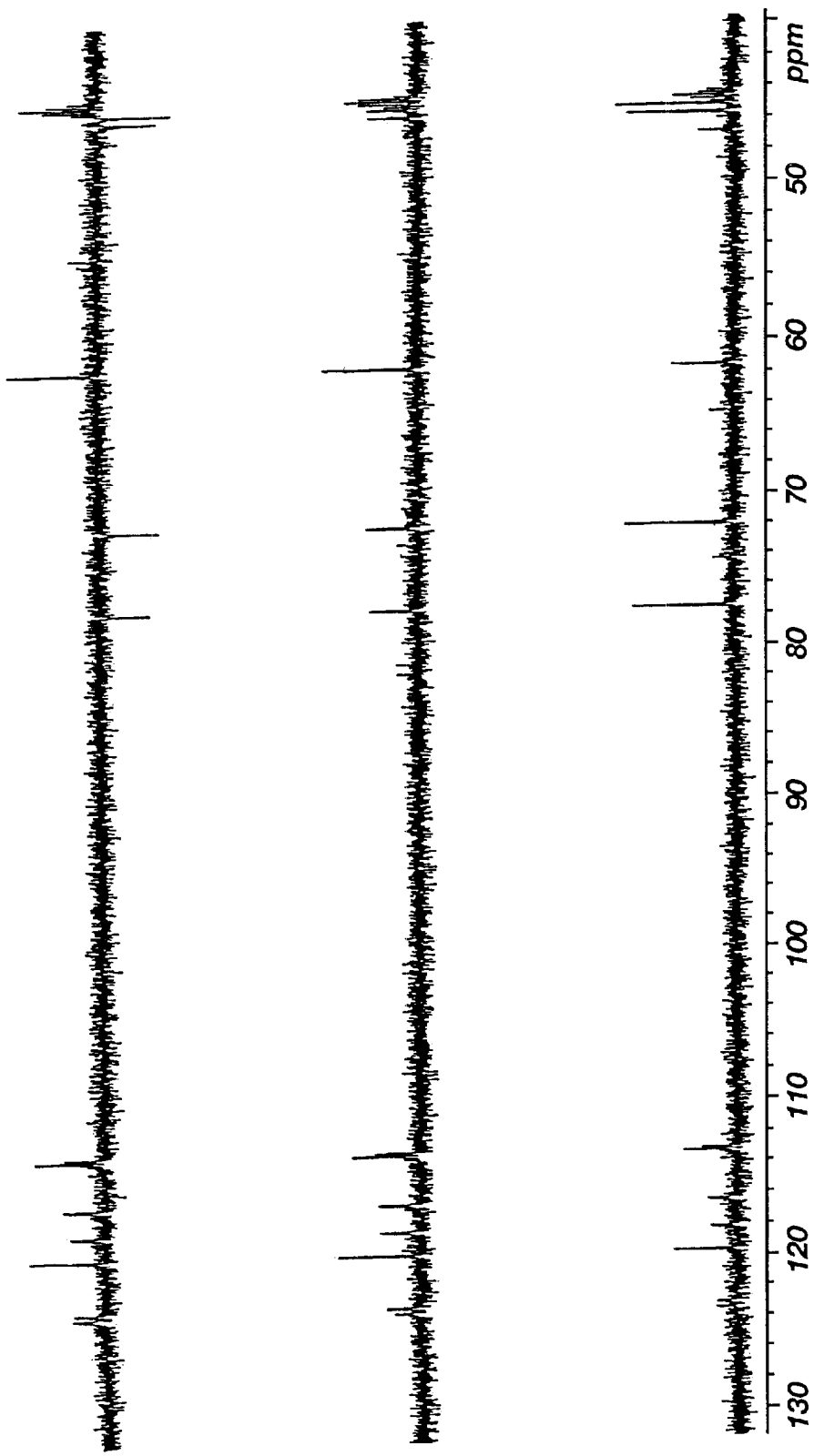
FIG. 4 shows a DEPT spectrum of the composition of the present invention.
Figure 5:
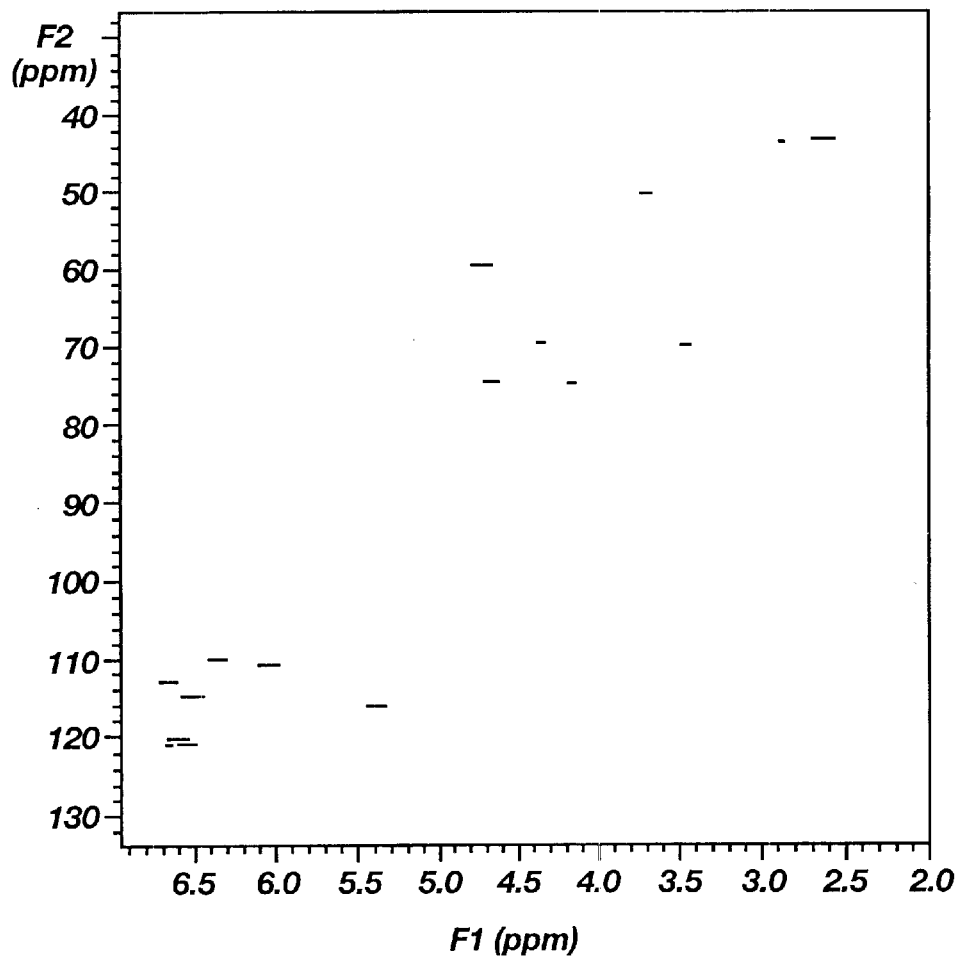
FIG. 5 shows a HETCOR spectrum of the composition of the present invention.

Analysis of the $^{13}$C spectrum obtained in DMSO-d$_6$ showed a total of 32 carbon resonances (FIG. 3, Table 1). Unlike haematoxyin, brazilin, and the Palo E compound (peak E of FIG. 1), the $^{13}$C spectrum showed a carbonyl carbon at 190.26 ppm. A downfield sp2 hybridized carbon was also observed at 165.49 ppm. A DEPT experiment exhibited 12 protonated carbons: 4 methylene and 8 methine. This result identified the remaining 20 carbons as quaternary (FIG. 4). HETCOR analysis confirmed results obtained from the DEPT experiment and allowed the connection of the carbons to their respective hydrogens (FIG. 5).

TABLE 1

| Carbon | $^{13}$Cδ (ppm) | DEPT | HETCOR | Comp. Est. |
|---|---|---|---|---|
| 1 | 113.964 | Q | — | 119.29 |
| 2 | 118.782 | T | 6.45 | 119.95 |
| 3 | 108.496 | T | 6.27 | 112.27 |
| 4 | 146.739 | Q | — | 146.79 |
| 5 | 133.203 | Q | — | 135.89 |
| 6 | 142.869 | Q | — | 144.76 |
| 7 | 67.361 | S | 3.24, 4.17 | 70.17 |
| 8 | 89.785 | Q | — | 73.73 |
| 9 | 40.883 | S | 2.77, 3.52 | 42.36 |
| 10 | 127.856 | Q | — | 125.68 |
| 11 | 111.868 | T | 6.544 | 111.84 |
| 12 | 144.779 | Q | — | 143.20 |
| 13 | 144.129 | Q | — | 146.24 |
| 14 | 113.531 | T | 6.346 | 117.44 |
| 15 | 136.596 | Q | — | 132.54 |
| 16 | 58.929 | Q | — | |
| 1' | 110.106 | Q | — | 120.58 |
| 2' | 118.450 | T | 6.45 | 119.47 |
| 3' | 108.679 | T | 5.89 | 113.16 |
| 4' | 147.999 | Q | — | 146.21 |
| 5' | 132.631 | Q | — | 134.43 |
| 6' | 144.517 | Q | — | 145.00 |
| 7' | 72.813 | S | 4.51, 4.01 | 72.14 |
| 8' | 73.908 | Q | — | 77.61 |
| 9' | 40.015 | S | 2.37, 2.46 | 37.27 |
| 10' | 127.261 | Q | — | |
| 11' | 102.419 | Q | — | |
| 12' | 146.736 | Q | — | |
| 13' | 165.479 | Q | — | |
| 14' | 190.255 | Q | — | |
| 15' | 115.018 | T | 5.229 | |
| 16' | 56.864 | T | 4.593 | 43.74 |

Figure 6:
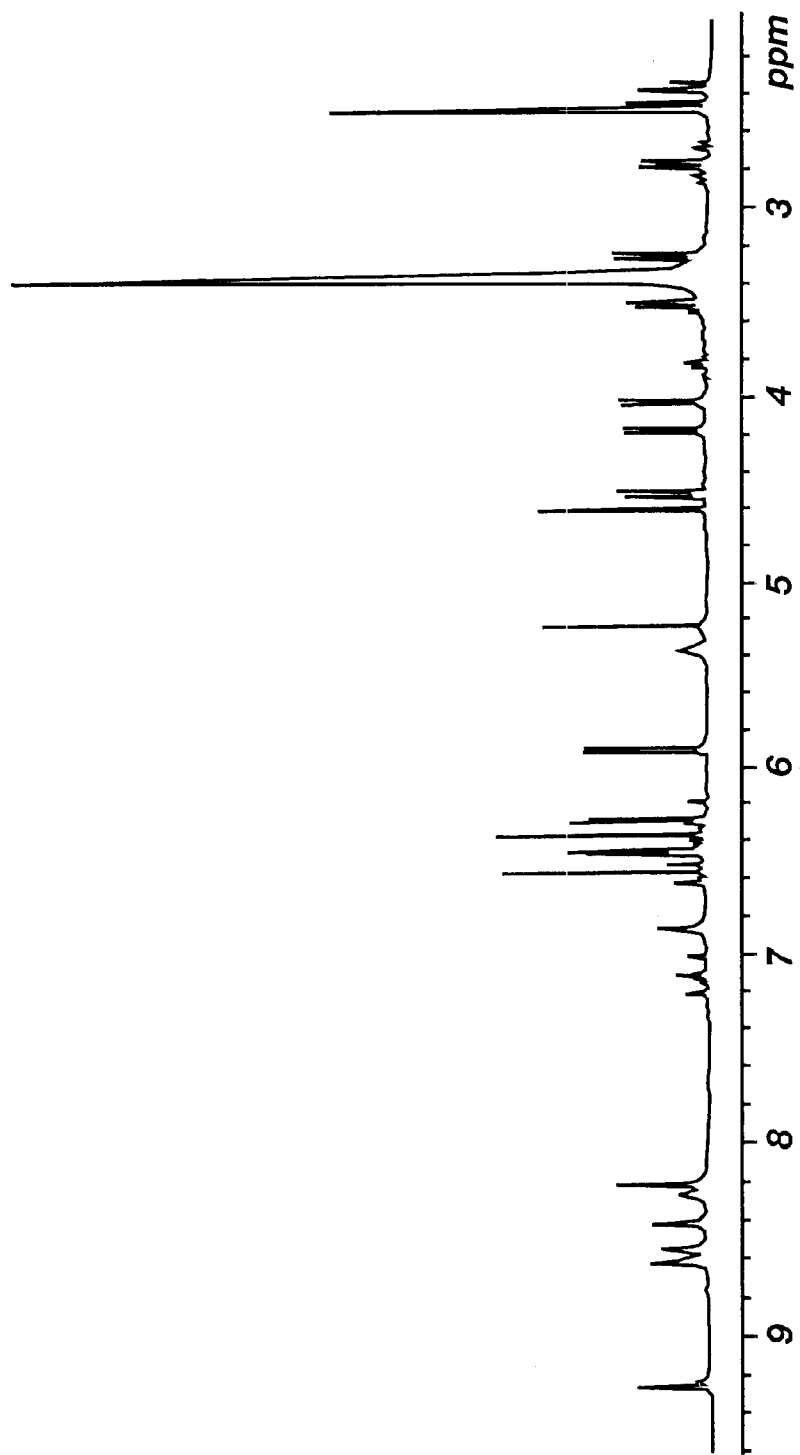
FIG. 6 shows a $^1$H spectrum of the composition of the present invention.
Figure 7:
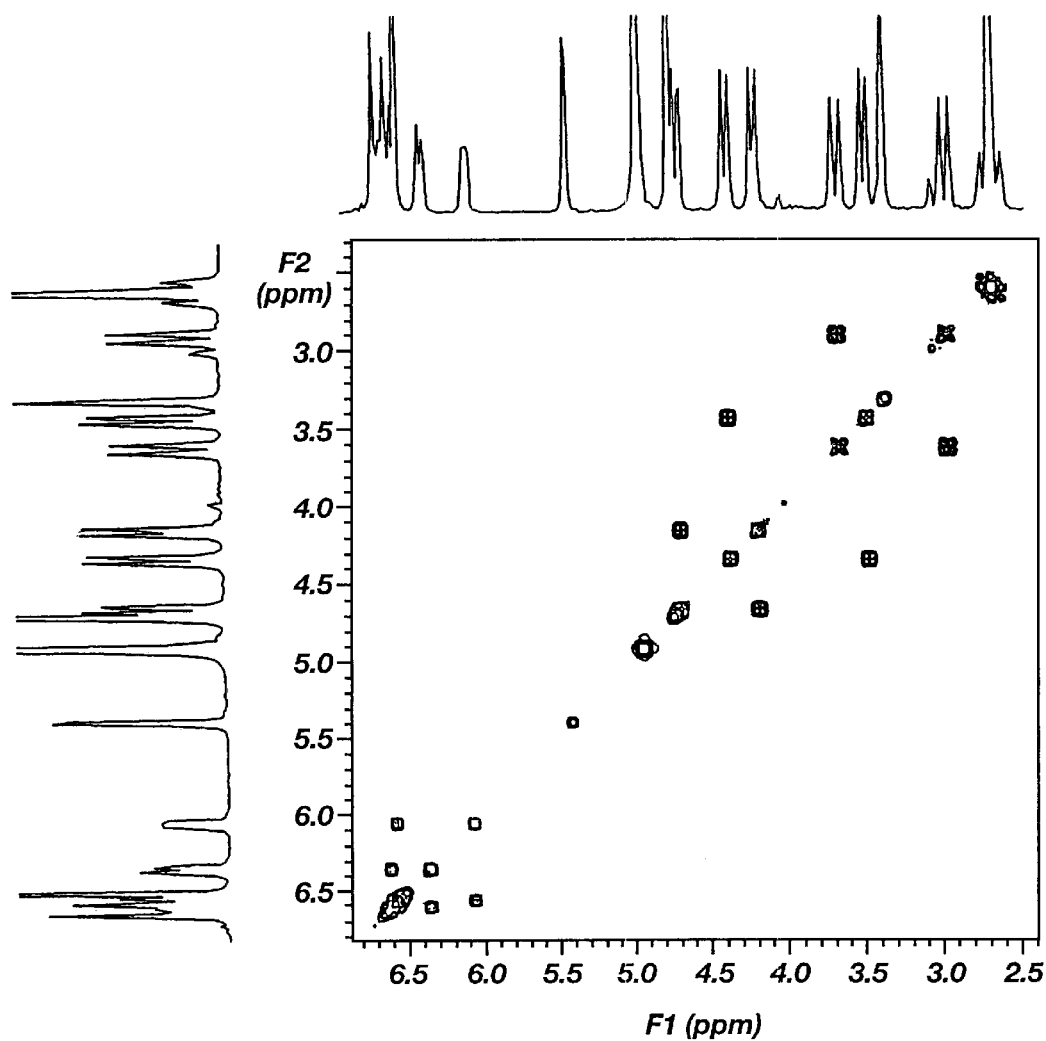
FIG. 7 shows a COSY spectrum of the composition of the present invention.
Figure 8:
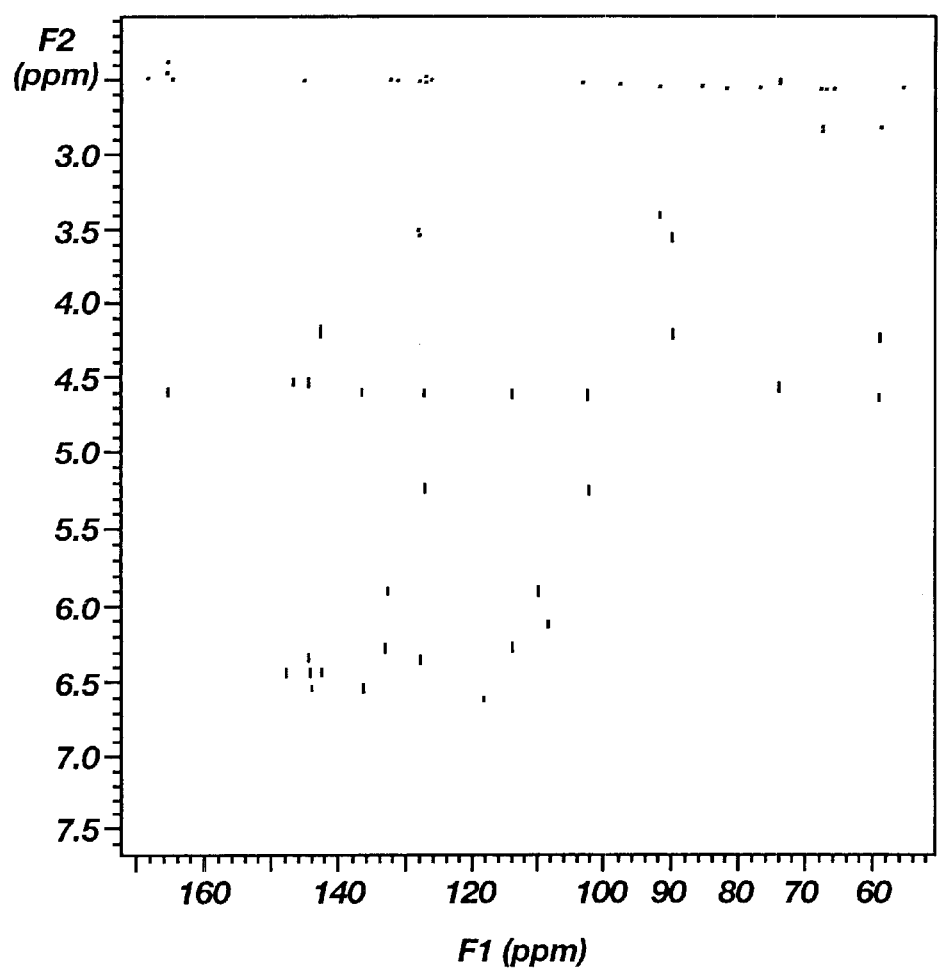
FIG. 8 shows an HMBC spectrum of the composition of the present invention.

A $^1$H spectrum in DMSO-d$_6$ showed 6 aromatic protons, 1 vinylic proton, and 9 aliphatic protons (FIG. 6). In addition, 6 phenolic hydroxyl groups resonating at 9.01, 8.71, 8.58, 8.44, 8.29, and 8.24 ppm and two hydroxyl groups at 6.93 and 5.38 ppm were also identified. A summary of non-exchangeable resonances and their respective couplings is shown in Table 2. Cross peaks as seen in the COSY spectrum confirmed all observed $^1$H couplings (FIG. 7).

TABLE 2

| Proton | δ (ppm) | J (Hz) | Coupled to Proton | Type of Coupling |
|---|---|---|---|---|
| 2 | 6.45 | 9 | 3 | ortho |
| 3 | 6.27 | 9 | 2 | ortho |
| 7a | 3.24 | 12 | 7b | geminal |
| 7b | 4.17 | 12.5 | 7a | geminal |
| 9a | 2.77 | 16.5 | 9b | geminal |
| 9b | 3.52 | 16.5 | 9a | geminal |
| 11 | 6.544 | — | — | — |
| 14 | 6.35 | — | — | — |

TABLE 2-continued

| Proton | δ (ppm) | J (Hz) | Coupled to Proton | Type of Coupling |
|---|---|---|---|---|
| 16 | 4.593 | — | — | — |
| 2' | 6.45 | 8.5 | 3' | ortho |
| 3' | 5.89 | 8.5 | 2' | ortho |
| 7'a | 4.01 | 11.5 | 7'b | geminal |
| 7'b | 4.51 | 11.5 | 7'a | geminal |
| 9'a | 2.37 | 17 | 9'b | geminal |
| 9'b | 2.46 | 17 | 9'a | geminal |
| ** | 5.229 | — | — | — |

This carbon is at 115.0 ppm.

All of these experiments were rerun in CD$_3$OD wherein all previously known peaks and cross peaks were observed.

Figure 9:
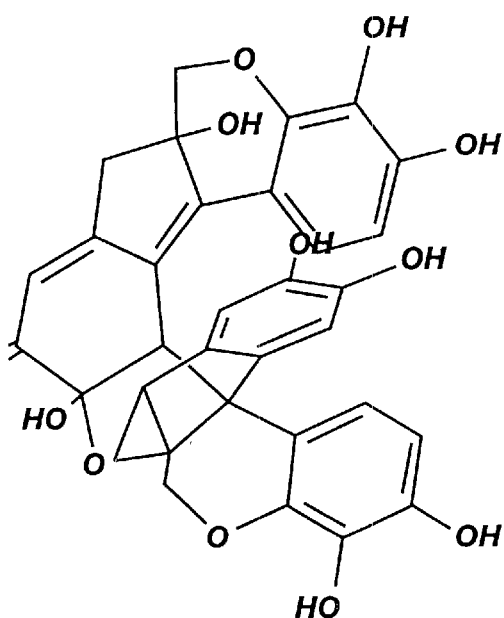
FIG. 9 shows the chemical structure of the composition of the present invention.
Figure 10:
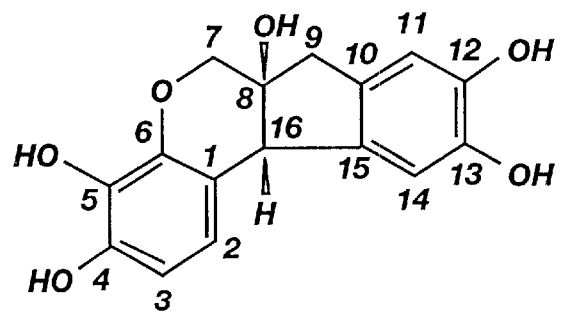
FIG. 10 shows the chemical structure of haematoxylin, a primary component of fraction B of FIG. 1.

The structure of Palo A is shown in FIG. 9. It appears to be a dimer-like compound formed from haematoxylin and a closely related compound. It has a unique acetal linkage between the two structural units. The structure of haematoxylin is shown in FIG. 10.

The subject matter claimed is:

1. A compound having the structure:

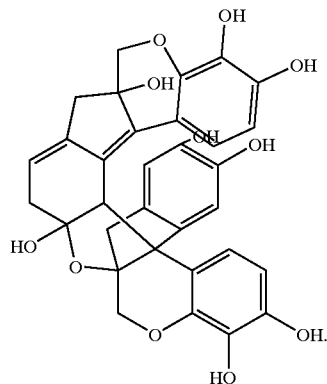

2. A method for isolating a compound having the structure:

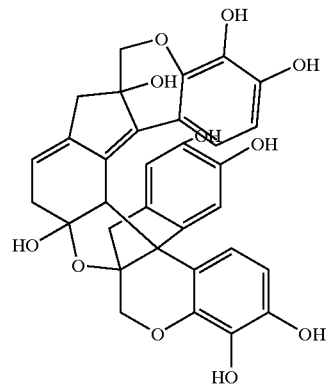

comprising:
 (a) obtaining an aqueous leachate from *Caesalpinia brasiliensis;*
 (b) fractionating the leachate by reverse-phase high pressure liquid chromatography; and
 (c) selecting a fraction substantially free of haematoxylin and having an activity for reducing blood pressure in hypertensive Sprague-Dawley rats.

3. The method of claim 2 wherein the aqueous leachate is from heartwood of *Caesalpinia brasiliensis*.

4. A method for treating hypertension in a mammal comprising the step of administering to the mammal an effective amount of a compound having the structure:

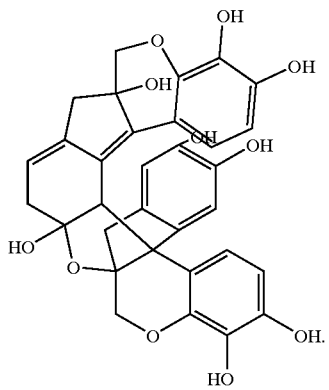

5. The method of claim 4 wherein the compound is isolated from *Caesalpinia brasiliensis*.

6. The method of claim 5 wherein the compound is isolated by:

(a) obtaining an aqueous leachate from *Caesalpinia brasiliensis*;

(b) fractionating the leachate by reversed-phase high pressure liquid chromatography; and (c) selecting a fraction substantially free of haematoxylin having an activity for reducing blood pressure in hypertensive Sprague-Dawley rats.

7. A composition comprising an admixture of an effective amount of a compound represented by the structure:

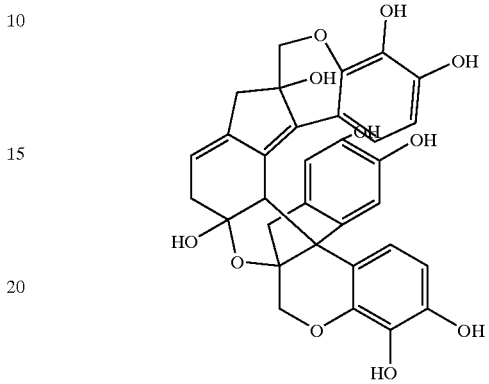

and a pharmaceutically acceptable carrier.

* * * * *